US005147283A

United States Patent [19]

Johnson

[11] Patent Number: 5,147,283

[45] Date of Patent: Sep. 15, 1992

[54] CUSTOM FINGER ATTACHMENT

[75] Inventor: John W. Johnson, Andrews AFB, Md.

[73] Assignee: The United States of America as represented by the Secretary of the Air Force, Washington, D.C.

[21] Appl. No.: 376,052

[22] Filed: Jul. 5, 1989

[51] Int. Cl.[5] ........ A61F 5/04

[52] U.S. Cl. ........ 602/7; 602/5; 128/846

[58] Field of Search ........ 128/87 A, 89 R, 845, 128/846, 878, 879, 880, 165; 602/1, 5, 7, 9, 14, 22

[56] References Cited

U.S. PATENT DOCUMENTS

| | | | |
|---|---|---|---|
| 2,646,794 | 7/1953 | Baer | 128/87 A |
| 3,741,207 | 6/1973 | Fuson | 128/879 |
| 4,220,334 | 9/1980 | Kanamoto et al. | |
| 4,615,522 | 10/1986 | Plough | |
| 4,619,250 | 10/1986 | Hasegawa | |
| 4,628,911 | 12/1986 | Bornstein | 128/879 X |
| 4,765,608 | 8/1988 | Bonasera | |
| 4,790,301 | 12/1988 | Silfverskiold | 128/87 A |
| 4,949,711 | 8/1990 | Gyovai et al. | 128/87 A |
| 5,020,524 | 6/1991 | Donohue | 128/87 A X |

OTHER PUBLICATIONS

Thermo-Mold Medical Products Inc., Ad for "Warm 'N Form" Orthopedic Device, 1974.

*Primary Examiner*—Robert A. Hafer
*Assistant Examiner*—Sam Rimell
*Attorney, Agent, or Firm*—Bobby D. Scearce; Donald J. Singer

[57] ABSTRACT

A finger attachment structure and fabrication method for connection to a passive motion machine or the like in the rehabilitation and therapy of the hand and fingers is described which comprises the steps of heating a sheet of low temperature formable plastic sized to enclose a selected plurality of fingers, folding an edge of the sheet over the selected fingers and carefully forming the sheet around individual fingers to produce a body member including a plurality of spaced cavities receiving and individually enclosing and separating the ends of the fingers to a preselected extent, cooling the body member to harden the plastic in the formed shape of the body member and attaching one or more loop members to the outer surface of the body member atop the finger cavities for receiving a bar member for connection to a machine for providing passive motion to the plurality of fingers.

4 Claims, 1 Drawing Sheet

CUSTOM FINGER ATTACHMENT

RIGHTS OF THE GOVERNMENT

The invention described herein may be manufactured and used by or for the Government of the United States for all governmental purposes without the payment of any royalty.

BACKGROUND OF THE INVENTION

The present invention relates generally to therapeutic and rehabilitative devices for the hand, and more particularly to a device for effective hand rehabilitation following surgery or other injury to a finger.

Post operative treatment for surgery on or other treatment for injury to fingers generally include a period of therapy or other rehabilitative treatment to the fingers and hand in order to restore to the extent possible a full range of muscle strength, coordination and range of movement. Such a procedure may involve use of therapy units such as a finger continuous passive motion machine (e.g., Sutter 5000, Sutter Biomedical Inc. San Diego Calif; or Kintec's Hand and Wrist Unit, Richard's Medical, Memphis Tenn). These machines are effective in enhancing hand rehabilitation in post-surgical, chronic and acute problems involving fractures, crush injuries and infections. In order to use a therapy machine effectively to rehabilitate a finger. suitable finger attachments must be supplied which provide positive and secure yet comfortable attachment to the machine and which allow the desired range of continuous passive motion. Previously existing structures for finger attachments have included simple tape tabs or Velcro TM tabs attached to the ends of each finger for receiving an attachment bar for the passive motion machine. These attachment structures have proved to be less than satisfactory in use because tape tabs provide minimal comfort and range of motion, cannot be sterilized and are subject to slippage on the finger in continuous use, and the Velcro TM tabs may cause substantial discomfort as a result of the degree of tightening needed to secure them to the fingers, cannot be sterilized and may be prohibitively expensive.

The invention described herein provides a finger attachment structure and method for making same particularly for use with finger continuous passive motion machines used for hand rehabilitation. The finger attachment is made from a low temperature formable plastic or like material custom fitted to one or more fingers, and includes formed loops for receiving an attachment bar for connection to a passive motion machine or the like. The attachment thus formed provides an inexpensive structure readily connectable to the continuous passive motion machine and allows full range of motion of the machine.

It is therefore a principal object of the invention to provide an improved finqer attachment structure for connection to a passive motion machine in the rehabilitation and therapy of the hand and fingers.

It is a further object of the invention to provide a method for fabricating an improved finger attachment for use in the rehabilitation and therapy of the hand and fingers.

These and other objects of the invention will become apparent as the detailed description of representative embodiments proceeds.

SUMMARY OF THE INVENTION

In accordance with the foregoing principles and objects of the invention, a finger attachment structure and fabrication method for connection to a passive motion machine or the like in the rehabilitation and therapy of the hand and fingers is described which comprises the steps of heating a sheet of low temperature formable plastic sized to enclose a selected plurality of fingers, folding an edge of the sheet over the selected fingers and carefully forming the sheet around individual fingers to produce a body member including a plurality of spaced cavities receiving and individually enclosing and separating the ends of the fingers to a preselected extent, cooling the body member to harden the plastic in the formed shape of the body member and attaching one or more loop members to the outer surface of the body member atop the finger cavities for receiving a bar member for connection to a machine for providing passive motion to the plurality of fingers.

DESCRIPTION OF THE DRAWINGS

The invention will be clearly understood from the following detailed description of representative embodiments thereof read in conjunction with the accompanying drawings wherein.

DETAILED DESCRIPTION

Figure 1:
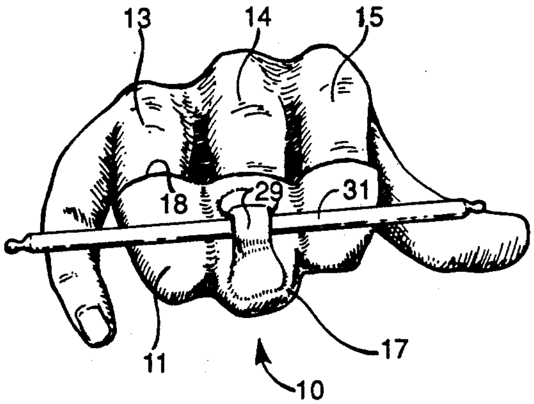
FIG. 1 is an illustration of a representative embodiment of a finger attachment of the invention configured for receiving three fingers.

Referring now to FIG. 1. shown therein is an illustration of a representative embodiment of a finger attachment 10 of the invention configured for receiving three fingers and fabricated according to the method hereinafter described. It is understood however that an attachment made according to the invention may accommodate single fingers or, more preferably, two, three or four fingers, as a particular application might require, as would occur to one with skill in the field of the invention guided by these teachings. Accordingly, attachment 10 comprises a form 11 custom molded to accommodate the desired number of fingers 13, 14, 15, one or more of which may previously have undergone surgery or otherwise may have been injured and in need of rehabilitation and therapy. Form 11 comprises a body portion 17 of low temperature formable plastic, elastomer or similar material (e.g. Polyform TM or PolyformII TM supplied by Smith & Nephew Rolyan, Inc. of Menomonee, Wis.) customarily used in removable splinting. Body portion 17 is formed to fingers 13, 14, 15 according to the method described hereinafter. Body portion 17 may optionally be formed with lining 18 of gauze or other suitable material as suggested below in the description of the method for forming body portion 17.

Figure 2:
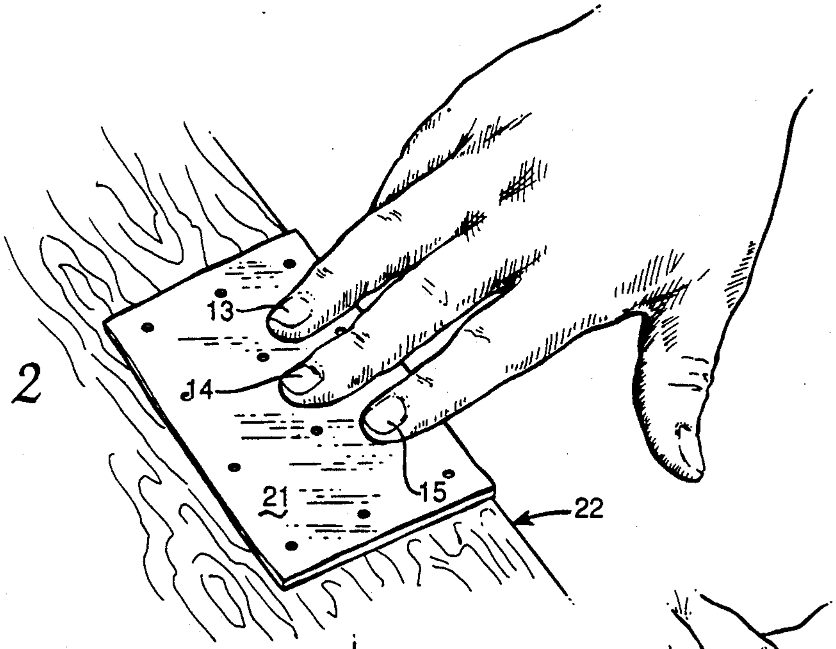
FIG. 2 is an illustration of the initial sizing of material for the FIG. 1 finger attachment and placement of three fingers thereon for fitting.

In fabricating attachment 10, plastic piece 21 of low temperature formable plastic sheet is provided of sufficient size (about six inches square, see FIG. 2) to accommodate the number of fingers (e.g. 13, 14, 15) to be received by form 11. Plastic piece 21 is first immersed in warm water (about 140°–170° F. for 1–3 minutes) for softening, dried and placed on a flat surface 22. Plastic piece 21 is then folded over and formed around the ends of fingers 13, 14, 15 so as to extend along the fingers to the finger joints for which hand/finger rehabilitation/therapy is intended. A suitable narrow tool 23 may be used to gently form plastic piece 21 around separated fingers 13, 14, 15 in the formation in body portion 17 of individual cavities 25, 26, 27 snugly receiving individual fingers 13, 14, 15 as suggested in FIG. 3. As suggested above, a lining of gauze or the like (not shown in FIG. 3) may be placed over plastic piece 21 prior to placement of fingers 13, 14, 15 thereon (FIG. 2) for formation of body portion 17. It is noted further that plastic piece 21 may be formed around fingers that are otherwise previously bandaged (not illustrated).

Figure 3:
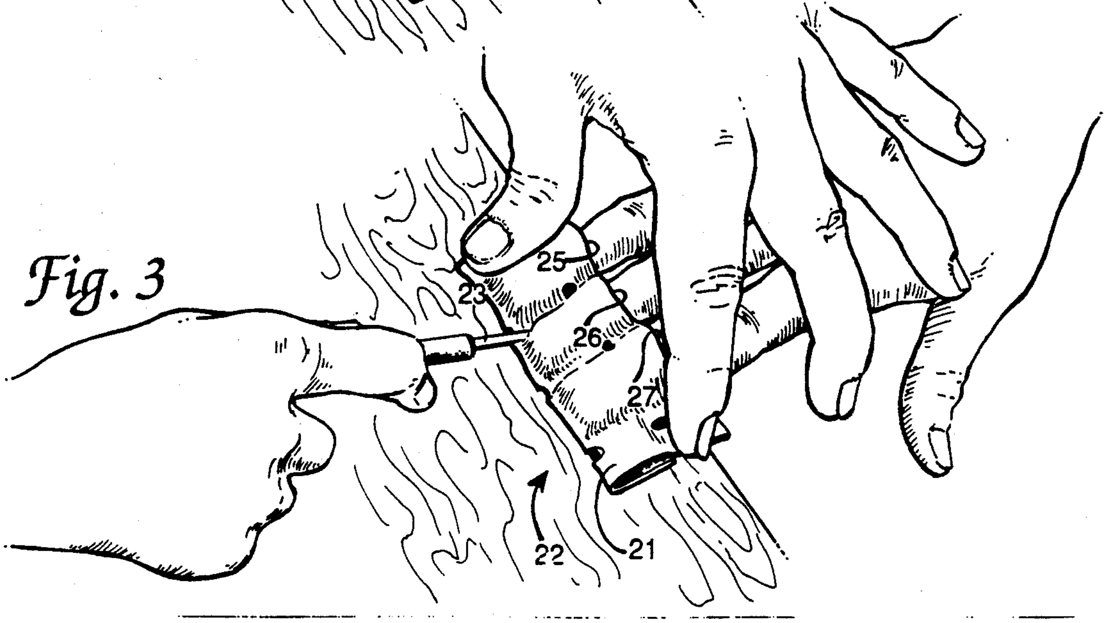
FIG. 3 is an illustration of the forming process for fitting the attachment of FIG. 1 over and around three fingers.

Plastic piece 21 as formed into the shape of body portion 17 as shown in FIG. 3 is then allowed to cool (as by water immersion) and harden, at which time the formed plastic body portion 17 may be removed from fingers 13, 14, 15. The formed body portion 17 is then trimmed to the shape of form 11 of FIG. 1 to enclose fingers 13, 14, 15 to a preselected extent just distal of selected finger joints intended for passive motion and rehabilitation. Trimming body portion 17 to the shape suggested in FIG. 1 allows for maximum range of motion when attachment 10 is placed into use according to the intended purpose. One or more retainer loops or hooks 29 (FIG. 1) are then formed, such as from small pieces (about 1×3/16 inch) of the formable plastic sheet, heated and softened and attached to body portion 17 at one or more positions atop respective finger locations within body portion 17. Loop(s) 29 are suitably formed and placed on body portion 17 for receiving bar 31 for attachment to a therapy unit, such as a Sutter 5000 CPM Unit (Sutter Biomedical Inc., San Diego, Calif.) which passively takes fingers of postoperative patients and those with a disability requiring movement over a specified range of motion for a selected period of time. Rough edges of body portion 17 may be dressed by hand using a heat gun. The completed attachment 10 with bar 31 inserted is then ready for use with a therapy machine.

It is noted that in the event attachment 10 loses proper fit during use as by swelling or loss of swelling in fingers 13, 14, 15, or by loosening of bandages on the fingers, the entire attachment may, if desired, be re-softened and re-fitted. The attachment may also be readily removed, sterilized and reapplied to the fingers without re-forming.

The invention therefore provides an improved therapeutic and rehabilitative device and method of making and using same for effective hand rehabilitation following surgery or other injury to a finger. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A method for making a finger attachment structure for connection to a passive motion machine or the like in the rehabiliatation and therapy of the hand and fingers, comprising the steps of:

(a) providing a sheet of low temperature formable plastic of preselected size sufficient to enclose a selected plurality of fingers of a hand;

(b) heating said sheet to soften said formable plastic;

(c) placing said selected plurality of fingers on said sheet;

(d) folding an edge of said sheet over said fingers to enclose said plurality of fingers to preselected extent;

(e) forming said sheet around individual said fingers to produce a body member defining a plurality of spaced cavities for receiving said plurality of fingers and individually enclosing and separating the ends of said plurality of fingers to said preselected extent;

(f) cooling said body member to harden said plastic in the shape of said body member; and (g) attaching a loop member to the outer surface of said body member atop a location correspondinq to the top of at least one of said plurality of fingers for receiving a bar member for connection to a machine for providing passive motion to said plurality of fingers.

2. The method of claim 1 further comprising the step of trimming said body member to size said cavities to enclose said plurality of fingers just distal of selected joints of said plurality of fingers.

3. The method of claim 1 wherein said heating step is characterized by heating said sheet to a temperature of about 140° to 170° F.

4. The method of claim 1 further comprising the step of applying a layer of gauze to said sheet prior to placing said selected plurality of fingers on said sheet and folding an edge of said sheet over said fingers.

* * * * *